United States Patent
Vija et al.

(10) Patent No.: US 11,642,093 B2
(45) Date of Patent: May 9, 2023

(54) CALIBRATION OF RADIATION DOSE ESTIMATION IN MEDICAL NUCLEAR IMAGING

(71) Applicant: Siemens Medical Solutions USA, Inc., Malvern, PA (US)

(72) Inventors: Alexander Hans Vija, Evanston, IL (US); Michal Cachovan, Baiersdorf (DE); Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 475 days.

(21) Appl. No.: 16/948,260

(22) Filed: Sep. 10, 2020

(65) Prior Publication Data

US 2021/0106302 A1  Apr. 15, 2021

Related U.S. Application Data

(60) Provisional application No. 62/912,843, filed on Oct. 9, 2019.

(51) Int. Cl.
*A61B 6/00* (2006.01)
*A61M 5/00* (2006.01)
(Continued)

(52) U.S. Cl.
CPC .............. *A61B 6/542* (2013.01); *A61B 6/037* (2013.01); *A61B 6/583* (2013.01); *A61M 5/007* (2013.01);
(Continued)

(58) Field of Classification Search
None
See application file for complete search history.

(56) References Cited

U.S. PATENT DOCUMENTS

| 8,577,103 B2 | 11/2013 | Vija |
| 8,675,936 B2 | 3/2014 | Vija |

(Continued)

FOREIGN PATENT DOCUMENTS

| EP | 1992965 A2 | 11/2008 |
| KR | 20100071593 A | 6/2010 |
| WO | 2019172997 A1 | 9/2019 |

OTHER PUBLICATIONS

Lin, et al. "Development of a patient-specific dosimetry estimation system in nuclear medicine examination," Advancements in Nuclear Instrumentation Measurement Methods and Their Applications (ANIMMA), 2011 2nd International Conference, IEEE, Jun. 6, 2011.

(Continued)

*Primary Examiner* — Hoon K Song

(57) ABSTRACT

For calibration of internal dose in nuclear imaging, the dose model used for estimating internal dose in a patient is calibrated. One or more values of the dose model (e.g., a physics simulation, dose kernels, or a transport model) are set based on measured dose. The dose may be measured relative to specific tissues and/or isotopes, providing for tracer and tissue specific calibration. For example, dose from the tracer to be injected into the patient is estimated from emissions as well as measured by a dosimeter in a tissue mimicking tissue mimicking object. These doses are used to calibrate the dose model, which calibrated dose model is then used to determine internal dose for the patient.

20 Claims, 2 Drawing Sheets

(51) Int. Cl.
G01T 1/24 (2006.01)
A61B 6/03 (2006.01)
(52) U.S. Cl.
CPC ............ G01T 1/24 (2013.01); A61B 6/032 (2013.01); A61B 6/463 (2013.01); A61B 6/5235 (2013.01)

(56) References Cited

U.S. PATENT DOCUMENTS

| | | | |
|---|---|---|---|
| 9,171,353 B2 | 10/2015 | Vija | |
| 9,332,907 B2 | 5/2016 | Vija | |
| 9,364,192 B2 | 6/2016 | Vija | |
| 9,910,162 B2 | 3/2018 | Bhattacharya | |
| 10,245,002 B2 | 4/2019 | Bhattacharya | |
| 10,828,004 B2* | 11/2020 | Conner | A61B 6/5205 |
| 2008/0272284 A1* | 11/2008 | Rietzel | G01T 1/29 250/252.1 |
| 2014/0371580 A1 | 12/2014 | Bhattacharya | |
| 2015/0196268 A1 | 7/2015 | Bhattacharya | |
| 2018/0092610 A1* | 4/2018 | Bhattacharya | A61B 6/037 |
| 2019/0038252 A1* | 2/2019 | Bhattacharya | A61B 6/5205 |
| 2019/0357872 A1* | 11/2019 | Ding | G01T 1/2026 |

OTHER PUBLICATIONS

Extended European Search Report in Corresponding Application No. 20200507.0, dated Feb. 9, 2021.

BIODEX "Dose Calibrators" https://m.biodex.com/nuclear-medicine/products/dose-calibrators pp. 1-2. Retrieved on Aug. 12, 2020.

PSTAR and ASTAR "Databases for Protons and Helium Ions" https//www.physics.nist.gov/PhysRefData/Star/Text/programs.html pp. 1-3. Retrieved on Aug. 18, 2020.

Stabin, M., and A. B. Brill. "Physics applications in nuclear Medicine: Progress on many fronts." The Journal of Nuclear Medicine 46.2 (2005): 16N.

Stabin, Michael G. "Update: the case for patient-specific dosimetry in radionuclide therapy." Cancer biotherapy & radiopharmaceuticals 23.3 (2008): 273-284.

Stabin, Michael G., and Jeffry A. Siegel. "Physical models and dose factors for use in internal dose assessment." Health physics 85.3 (2003): 294-310.

Stabin, Michael G., Richard B. Sparks, and Eric Crowe. "OLINDA/EXM: the second-generation personal computer software for internal dose assessment in nuclear medicine." Journal of nuclear medicine 46.6 (2005): 1023-1027.

Stabin, Michael. "Nuclear medicine dosimetry." Physics in Medicine & Biology 51.13 (2006): R187.

University of San Diego "Radionuclide Data Sheet" https://ehs.ucsd.edu/rad/radionuclide/Lu-177.pdf pp. 1-1. Retrieved on Aug. 18, 2020.

Watson, Evelyn E., Michael G. Stabin, and Jeffry A. Siegel. "MIRD formulation." Medical physics 20.2 Pt 2 (1993): 511-514.

* cited by examiner

CALIBRATION OF RADIATION DOSE ESTIMATION IN MEDICAL NUCLEAR IMAGING

RELATED APPLICATIONS

The present patent document claims the benefit of the filing date under 35 U.S.C. § 119(e) of Provisional U.S. Patent Application Ser. No. 62/912,843, filed Oct. 9, 2019, which is hereby incorporated by reference.

BACKGROUND

The present embodiments relate to emission tomography or nuclear imaging. An injected radiopharmaceutical emits radiation (in the case of single-photon-emission-computer-tomography (SPECT) imaging) or positrons that annihilate with electrons to produce radiation (in the case of positron-emission-tomography (PET) imaging). A detector system located outside the patient detects the emitted radiation and reconstructs images based on the detected emissions.

In theranostics, the radiopharmaceutical is used as a therapeutic agent. Emitted radiation applies a therapeutic dose to tracer-targeted tissue within the volume. Nuclear imaging is used to determine the dose applied to a patient. Internal dosimetry, such as medical internal radiation dose (MIRD), is the estimation of energy deposited to tissue due to uptake of the radioactive substance in the patient. Activity over time in the patient, such as from nuclear imaging of emissions from the patient at multiple timepoints (e.g., over a day or two), is reconstructed as distributions of the tracer within tissue over time. Using the reconstructed data, total decays, which relate to the total dose induced to the tissue, are computed. Simulated data exists for different isotopes and their energy lines to provide an estimate of the absorption of the radiation in the tissue, but a measured and calibrated standard for the various therapy tracers used in nuclear medicine is lacking. This results in a greater uncertainty of the estimated dose.

SUMMARY

By way of introduction, the preferred embodiments described below include methods, systems, instructions, and computer readable storage media for calibration of internal dose in nuclear imaging. The dose model used for estimating internal dose in a patient is calibrated. One or more values of the dose model (e.g., a physics simulation, dose kernels, or a transport model) are set based on measured dose. The dose may be measured relative to specific tissues and/or isotopes, providing for tracer and tissue specific calibration. For example, dose from the tracer to be injected into the patient is estimated from emissions as well as measured by a dosimeter in a tissue mimicking tissue mimicking object. These doses are used to calibrate the dose model, which calibrated dose model is then used to determine internal dose for the patient.

In a first aspect, a method is provided for calibration of internal dose in a nuclear imaging system. A solid-state detector detects emissions from a radiopharmaceutical to be provided in a patient. A solid-state dosimeter measures a first dose of the radiopharmaceutical. A dose model is calibrated with the first dose and a second dose derived from the emissions. The internal dose in a patient by the radiopharmaceutical is determined with the calibrated dose model.

In one embodiment, the emissions are detected from the radiopharmaceutical in a syringe or vial placed in a cavity. The first dose is measured with the solid-state dosimeter in a tissue mimicking object. The tissue mimicking object is in the cavity with the syringe or vial. In a further embodiment, the second dose is estimated from the emissions with the dose model. In calibration, a value of a parameter of the dose model is set so that a difference between the first and second doses is minimized. In another embodiment, the tissue mimicking object is a tissue-mimicking tissue mimicking object. The dose model is calibrated for a type of tissue mimicked by the tissue-mimicking tissue mimicking object. The dose model may be calibrated for an isotope to be used for the patient in the radiopharmaceutical and a type of tissue. The calibration may be repeated for different types of tissue so that the dose model has different settings for the different types of tissue. The internal dose is determined by type of tissue using the dose model as calibrated for each type of tissue.

Any of various types of dose models may be calibrated. For example, material dependent dose kernels are adjusted. As another example, a physics model is adjusted. In yet another example, a transport model is adjusted.

The internal dose may be determined for any time period. The absorbed dose in tissue of the patient is determined for a given period. In a further embodiment, an uncertainty of the internal dose is estimated and displayed with the internal dose.

To determine the internal dose, a nuclear imaging scan of the patient is performed at different times. In one approach, the internal dose by location is directly reconstructed with the calibrated dose model fit to data from the nuclear imaging scan in the reconstruction. In another approach, activity from detected emissions of the nuclear imaging scans for each of the times is reconstructed. The calibrated dose model is fit to the activities from the different times.

In a second aspect, a method is provided for calibration of internal dose in a nuclear imaging system. A first dose induced to a first type of tissue by a first isotope is measured. Dose estimation is calibrated to the measured first dose for the first type of tissue and the first isotope. A nuclear imaging system determines the internal dose for a patient with the calibrated dose estimation.

In one embodiment, emissions from a radiopharmaceutical in a syringe or vial are detected, and a second dose is estimated from the emissions using the dose estimation. The first dose from the radiopharmaceutical in the syringe or vial is measured with a solid-state dosimeter in a tissue mimicking object. The tissue mimicking object mimics the first type of tissue. In calibration, the dose estimation is altered based on the first and second doses.

In another embodiment, the dose estimation is a dose kernel model, a physics model, or an energy transport model. In calibration, a value of the dose kernel model, physics model, or energy transport model is set. The measurement and calibration may be performed for different types of tissue including the first type and/or different isotopes including the first isotope. In use of the calibrated dose estimation, emissions from the first isotope in the patient are detected. The calibrated dose estimation is fit to activities from the emissions.

In a third aspect, an emissions imaging system includes a tissue mimicking object with a solid-state dosimeter. The solid-state dosimeter is configured to measure ionizing radiation from an isotope, and the tissue mimicking object is configured to mimic a type of tissue. An image processor is configured to calibrate a dose model from the measured ionizing radiation. A nuclear imaging system is configured to determine an internal dose for a patient using the calibrated dose model.

In an embodiment, the emissions imaging system further includes a cavity configured to hold a syringe or vial and the tissue mimicking object. A semiconductor detector adjacent the cavity is configured to detect emissions from within the syringe or vial within the cavity. The image processor is configured to determine a first dose for the syringe or vial from the emissions and configured to calibrate based on the measured ionizing radiation and the first dose.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For physics-based modeling of dose, the simulation relies on Monte Carlo simulation without specific reference to the patient. While the simulations are correct and fundamentally backed-up with data, the application to image-based internal dose determination in the context of complex human anatomy and physiology is not as accurate or backed-up. In particular, radiation from beta emission do not fulfill the superposition principle well at small scales. Beta radiation is more dependent on the type of tissue, requiring more accurate calibration.

Monte Carlo simulations are costly, so often approximated with dose kernels. Dose kernels generally have sharp three-dimensional distributions, which are derived from one-dimensional analysis. For dose computation, the dose kernels are convolved spatially, implying that superposition holds. Charged particle energy loss is described by the Bethe formula and correspondingly energy transfer to the specific material is complicated and occurs on length scales of mm, i.e. in typical imaging pixels sizes. Energy loss of gamma radiation is described most prominently by photoelectric effect, Compton scattering and pair production, where the dose distribution follows an exponential model and is less dependent on small deviations of different tissue types in the body. Alpha radiation has such short ranges that it fulfills superposition on the length scales of interest. As therapy radiopharmaceuticals typically emit a spectrum of beta and gamma, and sometimes alpha, small scale dosimetry suffers from lack of calibration to specific isotopes and/or tissues.

To increase accuracy across the spectra, the radiation dose estimations are calibrated to a reference standard in theranostics. By using a physical measurement of the dose induced to tissue, the dose estimation may be calibrated to this standard. For example, calibrated dosimetry kernels are obtained based on measurements. The calibrated dosimetry kernels are applied to patient and system-specific data to obtain accurate dosimetry.

In one embodiment, a tissue mimicking object and dosimeter are used for the measurement of ionizing radiation induced by an isotope to the material/tissue mimicking object of interest to calibrate the dose estimation. For example, a mini-nuclear imaging system is employed to estimate dose from emissions using the dose estimation as well as to directly measure the dose before injection. The dose estimation is calibrated based on the measured dose and the estimated dose. The dose estimation may use any now known or later developed approaches, such as disclosed in multi-modal zoning (e.g., U.S. Pat. No. 9,332,907), reconstruction (e.g. U.S. Pat. Nos. 9,171,353; 8,675,936; or 8,577,103) and/or uncertainty estimation (e.g., U.S. Pat. No. 9,364,192).

Figure 1:
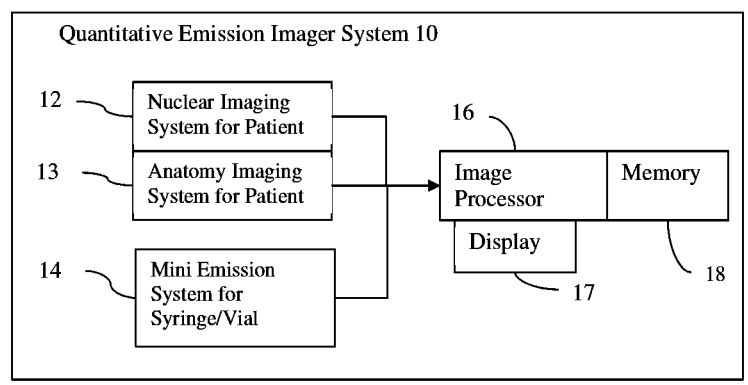
FIG. 1 is a block diagram of one embodiment of a quantitative emission imager system using a miniaturized emission system for dose model calibration.

FIG. 1 shows one embodiment of a quantitative emission imager system 10. The system 10 determines the internal dose to which a patient is subjected from a radiopharmaceutical. Sets of emission data from different timepoints or scans of the patient are used to estimate the internal dose. The internal dose is provided for confirming dosage in therapy and/or planning further therapy. The internal dose is determined by a dose model fit to reconstructed activity or used in a reconstruction of the dose. By reconstructing the dose rather than time specific uptake or tracer distribution, the dose applied to the patient during a therapeutic cycle or over multiple cycles is determined as an output of the reconstruction. In alternative embodiments, the dose is determined as a calculation from reconstructed activity over time.

The internal dose is determined, in part, from a dose model or dose estimation. The dose model is calibrated. To calibrate, the emission imager system 10 uses a direct measure of dose and an estimate of dose from the dose model. The direct measure of dose from a source may be measured using a dosimeter. The estimate of dose is from a scan of the source. In the example of FIG. 1, one or more tissue mimicking objects and one or more dosimeters for the measurement of ionizing radiation induced by an isotope to the material/tissue mimicking object are used to calibrate the dose estimation. For example, the radiopharmaceutical in the syringe or vial before injection to the patient is used as the source. The mini-emission system 14 performs PET or SPECT scanning to estimate the dose using the dose model. A dosimeter in a tissue mimicking object mimicking particular tissue or tissues directly measures the same dose. In other embodiments, the nuclear imaging system 12 estimates dose from a source and a dosimeter in a tissue mimicking object directly measures the dose. Alternatively, thermoluminescent detectors (TLDs) placed inside the body (implantable dosimeters) are used prior to treatment and extracted from the body after treatment to calculate absorbed dose. This method is invasive. TLDs may be placed on the surface, and dose in the body inferred, but this approach may be inaccurate since it uses uncalibrated dose kernels inside the body. Other dosimeter detectors include OSL (optically stimulated luminescence).

The system 10 includes an image processor 16, an emission imaging system 12, anatomy imaging system 13, a miniaturized emission system 14, a memory 18, and a display 17. Additional, different, or fewer components may be provided. For example, the anatomy imaging system 13 is not provided where dose is estimated without anatomical information. In one embodiment, the image processor 16, memory 18, and/or display 17 are part of one of the emission imaging system 12 or the anatomy imaging system 13. In alternative embodiments, the image processor 16, memory 18, and/or display 17 are provided as a workstation, server, or computer separate from the imaging systems 12, 14. The memory 18 is part of a computer or workstation with the image processor 16 or is a remote database, such as a picture archiving and communications system (PACS).

The anatomy imaging system 13 is a computed tomography (CT), magnetic resonance (MR), ultrasound, or other diagnostic medical imaging system. The anatomy imaging system 13 scans a patient with x-rays, ultrasound, or electric pulses to image the anatomy of the interior of the patient. A source transmits energy to the patient. A detector receives signals responsive to the transmitted energy. Any now known or later developed anatomy imaging system 13 may be used. While "imaging" or "image" is used herein, the anatomy imaging system 13 may be used to acquire anatomy data representing the patient without generating or displaying an image on a display device.

In one embodiment, the anatomy imaging system 13 is a CT system. An x-ray source and detector are mounted on a moveable gantry. The x-ray source generates x-rays, some of which pass through the patient. The detector detects the transmitted x-rays that pass through the patient. The energy used, timing, scan angles, and/or other aspects of the CT scan are set for a patient and used to scan a volume or other region of the patient. CT is used to generate a representation of the anatomy of the patient.

The emission imaging system 12 is any now known or later developed nuclear imaging system, such as a SPECT or PET scanner. The emission imaging system 12 includes a detector for detecting emitted radiation from within the patient. For SPECT, a gamma camera is used to detect. The detector detects photon emissions. A given detector may detect a sequence of events from the same or different locations of the patient. For PET, a ring of detectors and coincidence processor detect emissions.

The emission tomography system 12 is configured by software, firmware, and/or hardware to detect emissions. The emission tomography system 12 detects emissions from the same patient but during different imaging sessions. Each imaging session provides a complete scan of the patient, such as positioning a gamma camera at different locations relative to the patient and detecting emissions at each position during a dwell time. The patient may leave the emission tomography system 12 (e.g., get up off of the bed) between the different imaging sessions. The imaging sessions may be performed at different periods distributed over hours or days while the patient is being dosed by an internal radiopharmaceutical. The imaging sessions occur during a therapy cycle and/or over multiple therapy cycles. The imaging sessions may be over a period that is less than an entire cycle. For a same cycle, the patient is subject to therapy from a given application or dosage of a radiotracer during the different imaging sessions. For each cycle, a different application of the radiotracer is used.

The emission tomography system 12 (i.e., nuclear imaging system) is configured to determine an internal dose. The image processor 16 may determine the internal dose as part of the emission tomography system 12, even where the image processor 16 is separated from the rest of the emission tomography system 12. The internal dose for a patient is determined from detected emissions using a calibrated dose model.

The memory 18 is a random-access memory, graphics processing memory, video random access memory, system memory, cache memory, hard drive, optical media, magnetic media, flash drive, buffer, database, combinations thereof, or other now known or later developed memory device for storing data. The memory 18 stores detected emissions (e.g., PET or SPECT detected event data), signals from anatomy scanning (e.g., CT data), zone information, segmentation information, partial volume effect, smoothing filter coefficients, test activity, reconstructed activity, injected dose, internal dose, biodistribution, calibration, and/or reconstruction information. The memory 18 stores data as processed, such as storing a segmentation, calibration, forward projection of the assigned test activities, reconstruction from detected emissions, image objects, internal dose, a rendered image, and/or other information.

The memory 18 or other memory is a non-transitory computer readable storage medium storing data representing instructions executable by the programmed image processor 16 for determining dose or dose model calibration. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 17 is a monitor, LCD, plasma, touch screen, printer, or other device for displaying an image for viewing by a user. The display 17 shows one or more images representing internal dose, such as accumulated dose at a given time for a treatment cycle or total dose for one or more treatment cycles. Other images may be output, such as an image of function (i.e., representing the activity of the reconstructed object), such as uptake or activity concentration. The internal dose image is a quantitative image. The function image is a quantitative or qualitative SPECT or PET image. The image may be a volume rendering, a multi-planar reconstruction, a cross-section, and/or other image from a final image object. The image represents a distribution in the patient based on detected emissions from the emission imaging system 12. Uncertainty in dose estimation may be represented in the image.

The image processor 16 is a general processor, central processing unit, control processor, graphics processor, digital signal processor, application specific integrated circuit, field programmable gate array, amplifier, comparator, time-to-digital converter, analog-to-digital converter, digital circuit, artificial intelligence processor, analog circuit, timing circuit, combinations thereof, or another now known or later developed device for reconstructing from detected emissions, determining internal dose, and/or calibrating a dose model. The image processor 16 is a single device or multiple devices operating in serial, parallel, or separately. The image processor 16 is specifically designed or provided for internal dose determination or dose model calibration but may be a main or general processor of a computer, such as a laptop or desktop computer, or may be a processor for handling tasks in a larger system. The image processor 16 may perform other functions.

The image processor 16 is configurable. The image processor 16 is configured by software, firmware and/or hardware. Different software, firmware, and/or instructions are loaded or stored in memory 18 for configuring the image processor 16.

The image processor 16 is configured to calculate the internal dose applied to or absorbed by the patient. The internal dose may be estimated from the detected emissions from different times directly in parametric model reconstruction or from reconstructed activity distribution at different times. Multi-modal reconstruction may be used, such as using the anatomy information to reconstruct based, in part, on locations of different tissues.

In one embodiment, the image processor 16 is configured to reconstruct a distribution of the internal dose from the radiotracer by fitting a parametric or dose model of half-life of the radiotracer to the detected emissions. The radiotracer kinetics are modeled, such as including diffusion (e.g., k1 and k2 diffusion) in a transport model. The radiation transport and ionizing radiation energy deposition is modeled by a parametric model used in reconstruction. The parametric model may instead include Monte Carlo or dose kernels for emission determination. The generation of the object model from the emissions data uses, in part, the parametric or dose model. The dose model may provide different values for variables for different types of tissue as fit in the reconstruction. Alternatively, different parametric models are used for different types of tissue.

The image processor 16 is configured to determine the internal dose from the dose model. The fit dose model outputs the internal dose based on the input detected emissions from different time points and an injected dose. The internal dose is output as an accumulated dose. The fit dose model may be used to determine the accumulated dose at any time. The reconstruction directly determines the dose, providing a distribution of dose. Alternatively, the dose is calculated from reconstructions of activity at different times. Any dose calculation process may be used.

The image processor 16 is configured to calibrate the dose model. Rather than using dose estimation based on expected properties of the isotope and/or tissue, the dose estimation is calibrated. Measured ionizing radiation from the isotope to be used in the patient and an estimate of dose using the dose model are compared to determine a value or values of one or more settings of the dose model for the isotope and/or tissue(s). The dose model is adjusted so that the estimated dose matches the measured dose.

Any measure of dose and estimate of dose may be used. In the example below, the mini-emission system 14 and a tissue mimicking object 40 with dosimeters 42 (see FIG. 3) are used. In other examples, the emission tomography system 12 with a tissue mimicking object and dosimeter are used.

The image processor 16 is configured to acquire the injected dose or dose of the syringe or vial. For example, a dose calibrator is used to determine the dose to be injected. A user may enter the dose to be injected. Alternatively, the injected dose is determined from emissions detected using the mini-emission system 14 as described below for FIGS. 2A and 2B or from the direct measure by the dosimeter 42 as described for FIG. 3.

The image processor 16 uses the injected dose and the calibrated dose model to determine the internal dose of the patient from the emissions. The miniature emission imaging system 14 is used to calibrate the dose model. The miniature emission imaging system 14 may also be used as a dosimeter for medical nuclear imaging, such as to determine the injected dose.

Figures 2A, 2B:
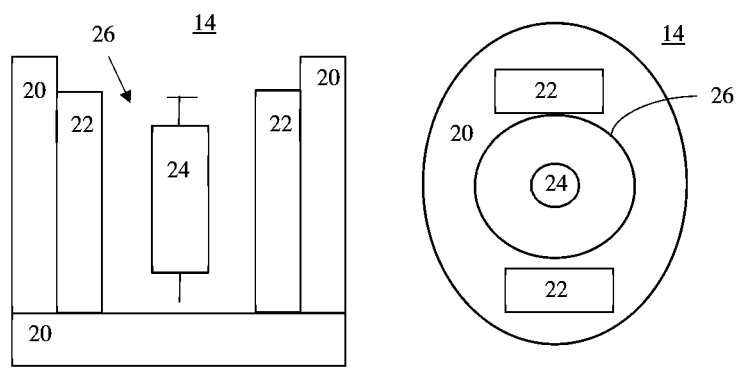
FIGS. 2A and 2B are side and top cross-sectional views of a miniaturized emission system.

FIGS. 2A and 2B show side and top cross-section views of the miniature emission imaging system 14. The system 14 includes side-walls 20 and one or more detectors 22 forming a cavity 26. Additional, different, or fewer components may be provided. For example, a gantry for moving the detectors 22 and/or collimators between the cavity 26 and the detectors 22 are provided. Collimators may be adjustable, such as automatically adapting to the isotope being used and/or patient treatment application. The collimator may be a rotating collimator and/or may cover any number of detectors 22. The collimator may provide step-wise or continuous aperture changes.

The side-walls 20 are shielding material to prevent or limit emissions from the syringe 24 or vial from passing out of the system 14. A lid, such as additional shielding may be provided. The shielding is lead or other material.

The detector 22 is a semiconductor detector. Any solid-state detector may be used, such as CZT, CdTe, HgI2, TlBr, GaAs, or other semiconductor materials. The semiconductor material has spectroscopic high energy resolution and may operate at room temperature or be cooled (e.g., cooling for HPGe detector).

One or more detectors 22 are provided. FIGS. 2A and 2B show two detectors 22 as flat substrates or plates on opposite sides of the cavity 26. Other shapes and/or arrangements may be provided. One, two, or more detectors 22 (emission sensors) are positioned inside the miniaturized emission imaging system 14. Additional, different, or fewer detectors 22 may be used, such as a ring of detectors around the cavity 26. The detectors 22 may be mounted to a gantry or other devices for moving the detectors 22. The gantry may move or the detectors 22 may be positioned based on images from scanning using the detectors 22 and/or based on an algorithm or artificial intelligence.

The detectors 22 are adjacent to the cavity 26, such as being within the cavity 26. The detectors 22 may be directly adjacent the cavity 26 or one or more layers of intervening material are provided, such as collimators. The detectors 22 are adjacent to the cavity 26 where the detectors 22 may detect emissions from within the cavity 26. The detectors 22 are configured (e.g., positioned) to detect emissions from within the syringe 24 or vial within the cavity 26.

The cavity 26 is cylindrical or prismoid. The cavity 26 is formed from the side-walls 20 and/or detectors 22. The cavity 26 is sized to hold a syringe 24 or vial. For example, the cavity 26 is sized to have an opening of 3×3 inches or less (e.g., 1-inch×1 inch or 2 inch by 1 inch) and sufficient height to enclose the syringe 24 or vial holding radiopharmaceutical for one or a few patient applications. The volume of the cavity may be less than 1 cubic foot.

Due to the small size of the cavity 26, the mini-emission imaging system 14 may have one or more handles placed on a housing or the shielding side-walls 20. The handle may be on a lid, which latches or screws onto the body to enclose the cavity 26. The overall size and weight may allow the system 14 to be carried, such as being the size of a 1-liter pitcher, 1-gallon jug, large coffee mug, briefcase, or luggage. The system 14 may be portable by being carried by one or two people. In other embodiments, the system 14 is fixed in place, such as being clamped or bolted to a floor, wall, or ceiling.

The syringe 24 or vial, such as a syringe 24 for a single dosage of radiopharmaceutical, may be placed into the cavity 26 through an opening, such as a top opening as shown in FIG. 2A. A holder, such as a plastic holder, may be provided. Alternatively, the cavity 26 is sized to hold the syringe 24 or vial upright or resting on its side with a pressure or frictional engagement. The syringe 24 or vial is positioned in the cavity 26 for PET or SPECT scanning using the detectors 22.

The image processor 16 is configured to determine the activity and/or dose from the radiopharmaceutical in the syringe 24 or vial. The radioisotope of the radiopharmaceutical emits radiation or positrons that result in generation of ionizing radiation, such as alpha, beta, and/or gamma rays. Some of these emissions are detected by the detectors 22. The image processor 16 counts the detected emissions. The locations of the emissions (e.g., lines of response) may be recorded. For PET, the coincidence (e.g., matched timing from two detectors on opposite sides of the syringe 24) may be determined and recorded with the lines of response. The energy level of the emissions may or may not be recorded. An emission scan of the syringe 24 or vial is performed, and the image processor 16 determines the activity or dose from the emissions scan.

The image processor 16 is configured to determine the dose from activity over time. The dose may be reconstructed, such as including the dose model in the reconstruction from emissions at different times. Alternatively, the activities at each of multiple times are reconstructed. The dose is determined from the reconstructed activities using the dose model. The reconstruction is the same as the reconstruction to be used on the patient and provides a two or three-dimensional distribution of activity or dose. Alternatively, the image processor 16 uses a pseudo-imaging reconstruction that integrates the counts of emissions to provide a global dose and/or activity (e.g., count over an area or volume) without determining a spatial variation or distribution of the activity or dose.

The mini-emission imaging system 14 may be used to determine activity and/or dose for the syringe 24 or vial before and after injection. The differences in activity or dose indicate the injected activity and/or injected dose. Alternatively, the dose in the syringe 24 or vial is measured just before or just after the injection without determining a difference for the injected dose.

The mini-emission imaging system 14 is used to calibrate the dose model. The generic function of uptake and washout of the radiopharmaceutical is a shark-fin like function, which is not known for an individual and depends on the specific individual and radiopharmaceutical injected. The internal dose is determined, in part, by modeling this generic function. Various dose models may be used, such as a physics model (e.g., ray tracing or Monte-Carlo-based model), a model formed from dose kernels, or a transport model of in-flow and out-flow (e.g., diffusion model).

One or more characteristics of the model are set in calibration. To calibrate, the dose from the syringe 24 or vial is determined by the emission scan using the dose model.

Figure 4:
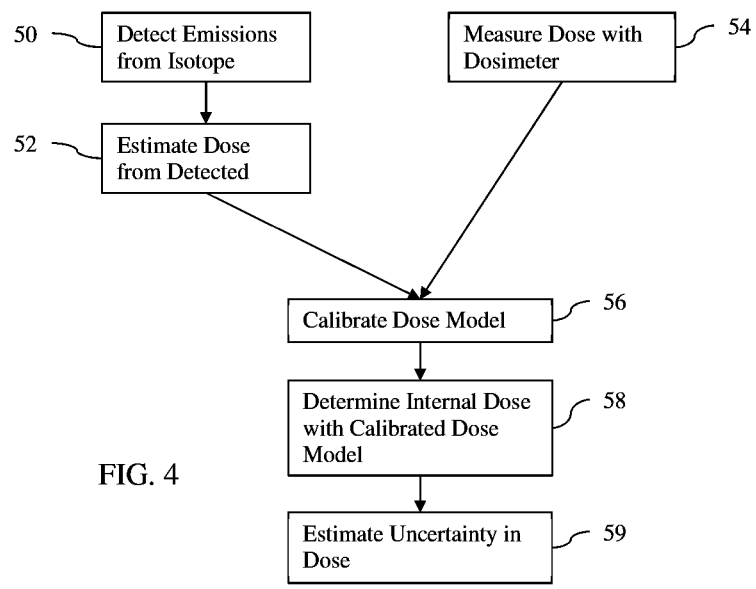
FIG. 4 is a flow chart diagram of one embodiment of a method for calibration for internal dose.

The actual dose is measured using a solid-state dosimeter, such as a diamond detector in a tissue mimicking object, at the same time or a different time than the emission scan. The signals from the solid-state dosimeter are used to determine the actual dose. The two doses are compared. The setting for the dose model that minimizes the difference in the two doses is found, calibrating the dose model. Since the calibration is based on the radiopharmaceutical to be used with the patient and the dose model to be used to determine internal dose for the patient, the calibration may be accurate. FIG. 4 shows one embodiment of a method for calibrating the dose model. In alternative embodiments, the estimated dose and measured dose for calibration are based on measurements of another source instead of the syringe 24 or vial and/or based on measurements by another device than the mini-emission system 14.

The mini-emission imaging system 14 is used to determine the injected dose for a particular patient or instance. By directly measuring activity in a syringe or vial using a solid-state detector, a dose may be determined. The emission imaging system 14 allows for dose determination with more accuracy than a gas chamber dosimeter and with less need for calibration with multiple standardized, calibrated sources.

The mini-emission imaging system 14 measures the activity of a radiopharmaceutical in a syringe 24 or vial. The syringe 24 or vial holding the radiopharmaceutical to be injected into the patient is placed in the cavity 26. The cavity 26 is sized to hold the syringe 24 or vial and may be small such that a patient cannot be placed in the cavity 26. This measurement is of the activity and/or dose for the isotope being used in the patient. After sealing the syringe 24 or vial in the cavity 26 (e.g., placing a lid over the cavity 26), the emissions are detected as the measure of activity.

To measure the activity, a PET or SPECT scan is performed. The mini-nuclear imaging system 14 scans for emissions from the radiopharmaceutical in the syringe 24 or vial. In one embodiment, the activity in the syringe 24 or vial is directly measured by the semiconductor detectors in a single measurement by combining direct photon measurements (e.g., spectrum and number of counts per energy bin) and extra modal information of the syringe or vial given another device, i.e., a camera, IR camera/sensor, etc.). A CT scan is not needed since there is a limited number of syringes or vials and an AI algorithm, for instance, can identify which syringe is being used and its position inside the chamber for precise activity calculation in the syringe pre- and post-injection for every patient. The measurement using the mini-nuclear imaging system 14 scans the radiotracer before and after injecting it in the patient, but after that, the PET/SPECT scanner 12 scans the patient. Multiple scans are performed over time for the patient. Using this approach, fewer scans and/or more accurate dose estimation will occur. Multiple sets of emissions from the patient are detected at multiple timepoints. Separate scans are used for each of the timepoints. Emissions are detected, such as with a complete SPECT or PET scan, for each of the timepoints. Where the same syringe 24 or vial is used multiple times (for the same patient or different patients), the later occurring uses already have activity measured, so the measurement to determine injected activity occurs after injection for the subsequent patient.

The emission imaging system 14 detects emissions from the radiopharmaceutical in the syringe 24 or vial with the detector 22 over time, such as over tens of seconds. A collimator in front of the detector 22 limits the direction of photons detected by the detector 22, so each detected emission is associated with an energy and line or cone of possible locations from which the emission occurred for SPECT scanning. The lateral position of the line or cone relative to the detector may likewise be determined. For PET scanning, coincidence processing may be used to detect a line of response for co-occurring emissions traveling in generally opposite directions. In alternative embodiments, the detection is performed without location determination (e.g., without a collimator). The counts are integrated into a global activity provided without spatial reconstruction (i.e., pseudo-imaging approach).

For the SPECT or PET scan, raw emission data is used for reconstruction. The reconstruction may use a system matrix or projection operators to describe the properties of the mini-emission imaging system to iteratively improve a data model of an image object representing the activity. The detected emissions are reconstructed to show spatial distribution of activity. Where the dose is reconstructed, the activities over the different time points are used to reconstruction dose. The activities are reconstructed as part of reconstruction of the dose.

The image object, which is defined in an object or image space, is a reconstruction from the emission data measured in a data space. The object space is the space in which the result of the image reconstruction is defined and corresponds, for example, to the 3D volume or 2D area (i.e., field-of-view or "FOV") that is imaged. The detected emissions form projections, which may be tomographically computed to represent two- or three-dimensional distribution by reconstruction. The reconstruction uses emissions detected from different directions or camera locations in each set of emissions.

The tomographic reconstruction iteratively fits the detected emissions to a distribution of the radiopharmaceutical in the object or image space. Iterative optimization is applied to find the distribution that best fits the measured emissions. Backward and forward projection from the detection space and the object space are used as well as any modeling, such as the system model for the emission tomography system (e.g., detector sensitivity) and/or a parametric dose model for kinetics of the radio tracer (e.g., diffusion in two directions (e.g., k1 and k2) with decay). In an iterative optimization, a model of the emission tomography system is used to forward project measurements to object space, and residuals are back projected for correcting a data model for the next iteration.

The image processor 16 may determine the injected dose. The injected dose is determined from the measured activity in the syringe 24 or vial before and after injection. The dose before injection is determined, and the dose after injection is determined. The difference in doses is the injected dose. Alternatively, the dose before or the dose after injection is used without determining the injected dose.

Where the measurements of activity are of the emissions, then reconstruction of the activity and/or dose is performed to determine the dose. The dose may be determined in one reconstruction from emissions from the multiple time points. The reconstruction is parametric, including the dose model fit as part of the reconstruction. Where activity is reconstructed, then the dose is determined from the activity over time by fitting the dose model to the reconstructed activity over time.

Any dose model may be used. The dose model may be a parametric model of pharmaceutical kinetics, such as diffusion, isotope half-life, biological half-life, and/or another characteristic of change over time in dosage being applied from the radiopharmaceutical. A physics model, such as using Monte Carlo, dose kernels as the model, or a transport model may be used to model emission probability and/or interaction for dose. Based on fitting, values of the model parameters of the dose model are solved, providing dose for any time and/or total dose for the locations of the distribution. As an example of a transport-based dose model, a 2-compartemental model is encapsulated in a set of linear differential equations, whereby the k12, . . . are kinitic parameters for moving from compartment 1 to compartment 2. Generally, the compartment can be a voxel or a volume of interest (VOI). By solving for the fit of the model of radiopharmaceutical kinetics, the dose may be determined. The dose or dose distribution is determined. The distribution is by voxel.

Figure 3:
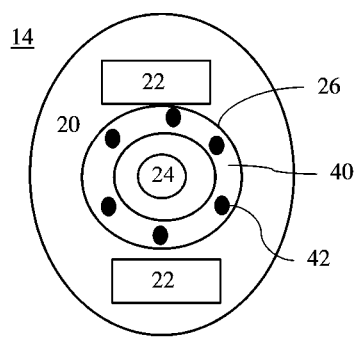
FIG. 3 is a cross-section top view of a miniaturized emission system with a tissue mimicking object having solid-state dosimeters for dose model calibration.

For calibrating the dose model, the same dose is measured by a dosimeter. The mini-nuclear imaging system 14 may be used to calibrate the dose model used in reconstructing the injected and/or internal dose. FIG. 3 shows the mini-nuclear imaging system 14 with a tissue mimicking object 40 included in the cavity 26. The tissue mimicking object 40 mimics tissue of interest, such as blood, soft-tissue, or bone. For example, a water bath is used for blood. As another example, soft-tissue or bone mimicking plastic is used. The same or different tissue mimicking objects 40 may be used to mimic different tissues. Multiple objects 40 for multiple different tissues may be used. One object 40 may mimic different tissues. The object 40 has known attenuation and/or attenuations corresponding to the tissue being mimicked.

The tissue mimicking object 40 is positionable within the cavity 26. The object 40 has a known position and orientation. As shown in FIG. 3, the tissue mimicking object 40 has an outer surface sized and shaped to confirm with the surface of the cavity 26. In other embodiments, the tissue mimicking object 40 fits with less or no contact with the side walls, bottom, and/or top of the cavity 26, such as being held in the cavity 26 by one or more spacers or holders.

The tissue mimicking object 40 includes one or more solid-state dosimeters 42. For example, diamond detectors are used as the solid-state dosimeters 42. The solid-state dosimeters 42 are configured to measure ionizing radiation from an isotope, such as the radiopharmaceutical to be injected into the patient. Other semiconductor detectors for directly measuring the dose may be used. Any number and any spacing of the dosimeters 42 may be provided.

The tissue mimicking object 40 includes an inner chamber into which the syringe 24 or vial is placed and held. The solid-state detectors 22 are used to measure activity, from which dose is determined. The dosimeters 42 measure the dose from the syringe 24 or vial at a same time or times as the detectors 22 detect emissions or over an equal but different period.

The image processor 16 calibrates the dose model using any difference in doses. The estimated dose from emissions is compared to the directly measured dose from the dosimeters 42 of the tissue mimicking object 40. The dose model is weighted or adjusted to result in the directly detected dose from the dosimeters 42 given the measured activity from the detectors 22. The dose model is calibrated from the signals from the solid-state dosimeter 42.

FIG. 4 shows a flow chart diagram of a method for calibration of a dose model and use of the calibrated dose model in a nuclear imaging system. The calibration is incorporated into the reconstruction and dose estimation process. In one embodiment, solid-state dosimeters 42 (e.g., diamond detectors) in a bath or another tissue mimicking object 40 are used to estimate the dose given the amount of activity present, allowing for the calibration of image-based dosimetry to be as accurate as existing methods with less or no need of user intervention. The tissue mimicking object 40 and included dosimeter 42 are used to calibrate the transport, physics, or dose kernel-based dose model used for determining the internal dose of the patient.

The acts are performed in the order shown (numerical or top to bottom) or another order. For example, acts 50 and 54 are performed simultaneously or sequentially with act 50 first or with act 54 first.

Additional, different, or fewer acts may be used. For example, act 58 and/or act 59 are not performed. As another example, acts for emission scanning a patient, such as with PET or SPECT imaging system 12 and/or acts for imaging anatomy by the anatomy imager 13 for multi-modal reconstruction and/or attenuation are performed. In yet another example, acts 50-56 are repeated for each of different types of tissue and/or isotopes. Different tissue mimicking tissue mimicking objects 40 are used to calibrate the dose model by tissue type.

In act 50, emissions from a source are detected. The source uses the same isotope to be used with the patient. For example, the emissions are detected from the radiopharmaceutical to be injected into the patient. In other examples, the emissions are from another source, such as a standard or calibrated source.

The emissions are detected with a solid-state detector. The solid-state detector may be part of the nuclear imaging system or a different system (e.g., mini-emissions imaging system 14). In one embodiment, the solid-state detectors 22 detect emissions from the radiopharmaceutical to be injected into a patient. The syringe 24 or vial is placed in the cavity 26 and in or beside the tissue mimicking object 40. The activity is measured by the detectors 22 while the tissue mimicking object 40 is in the mini-nuclear imaging system 14 with the syringe 24 or vial. Alternatively, the activity is measured without the tissue mimicking object 40 being in the cavity, which tissue mimicking object 40 is used at a different time. In other alternatives, other detectors than solid-state detectors are used.

In act 52, the image processor estimates the dose from a reconstruction of activity over time of the detected emissions. A representation of the object 40 is reconstructed from the detected emissions. The known attenuation and position of the object 40 may be used in the reconstruction. The activity distribution may be reconstructed for different times and the dose model fit to the reconstructed activity over time. Alternatively, parametric reconstruction is performed to fit the dose model to the activity from emissions over time. In yet other embodiments, activity from one time is used to fit the dose model. In these approaches, dose estimation is performed based on the detected emissions and the dose model.

The dose model of the time activity curve is fit to the emissions over time to compute the dose (e.g., energy/mass or J/kg (Gy)). The dose function, D, is a function of time and is different from activity, A=Bq. For dose tomography (i.e., fitting the dose model as part of one reconstruction), the available data from the 1 . . . N timepoints are used to describe a dynamic process and specify what moment of the spatial distribution is desired. The 1 to N timepoints are used in one reconstruction to parametrize dose distribution. Instead of computing the quantitative activity at each time point, the tomographic data from multiple (e.g., all) available time points is used to directly reconstruct the dose. For example, a spatio-temporal inconsistent SPECT, where the tomographic dwell time the dwell T_D<<T_R (residence time of the radiopharmaceutical) and assuming that the activity is constant or only slowly changing over T_D as compared to T_R, measures at the different timepoints. The dose in the target volume is reconstructed directly in a parametric approach. In this parametric reconstruction approach, the error propagation is seamless, and the noisy voxels at the later times are naturally stabilized. This parametric approach provides a fit model of dose, that may extend to temporal consistent nuclear imaging systems and T_D<< or just < than T_R. In alternative embodiments, the activity distributions at different times are reconstructed. The dose model is fit to the activities over time.

In an alternative embodiment, the spectrum information from the detected emissions is used to determine the isotope. The dose is estimated from the isotope and the emissions without reconstruction. Interpolation may be used to determine the dose from the spectrum.

Any dose model may be incorporated into reconstruction as the parametric dose model. Any dose model may be fit to reconstructed activities in the alternative embodiment. Example dose models include a dose kernel model, a physics model, or an energy transport model.

In act 54, a dose from the same source is measured. Rather than relying on estimation using the dose model and emissions, the dose is directly measured. A dosimeter directly measures the dose. For example, a diamond detector or other solid-state dosimeter measures the dose.

The dose induced to a particular type of tissue by a particular isotope is measured. The dosimeter may be embedded in a material, such as a plastic tissue mimicking object, actual tissue, and/or other material. The measure of dose is relative to the tissue of interest, such as measuring dose for soft tissue, bone, and/or fluid. The source of the ionizing radiation is a particular isotope or combination of isotopes, such as the isotope to be injected into the patient. The dose is measured for the tissue and/or isotope used for imaging the patient.

In one embodiment, the solid-state dosimeters 42 of the tissue mimicking object 40 measure the dose of the syringe 24 or vial. The tissue mimicking object 40 is in the cavity 26 with the syringe 24 or vial to measure the dose. The image processor 16 uses the signals from the solid-state dosimeters 42 to determine the dose for a same length of time as the dose determined in act 52. The tissue mimicking object 40 mimics the tissue of interest, such as soft tissue.

In act 56, the image processor calibrates dose estimation. The measured dose for the type of tissue and the isotope as well as the estimated dose from emissions are used to calibrate the dose model. For example, the image processor 16 calibrates the dose model with the measured dose from the solid-state dosimeter 42 and the estimated dose derived from the emissions detected by the solid-state detectors 22.

One or more values or weights of the dose model are set based on a difference between the estimated dose and the measured dose. An optimization may be performed to set one or more variables based on the difference in dose. The optimization minimizes the difference between the doses by setting the value or values of one or more variables of the dose model. The dose estimation is altered based on the measured and estimated doses. The value or values are set so that a difference between the first and second doses is minimized.

In other embodiments, the measured dose and the isotope from the spectrum of the emissions is used to calibrate the dose model. A library of dose models is provided for different isotopes and measured dose. By selecting or interpolating, a dose model calibrated for the isotope and tissue being mimicked is selected.

The dose model is a physics, dose kernel, or transport (transfer) model. For example, the dose model is formed by material-dependent dose kernels. The dose kernels may be anchored by measurements or simulation for the specific type of radiation and material (e.g., dose-specific zone map from tissue segmentation). For the tissue of interest, the dose kernel amplitude, variance, or other characteristic are adjusted in the calibration. In another example, the dose model is formed as a physics model of energy deposition. Raytracing and/or any type of accelerated Monte Carlo-based estimation of energy deposition is used. The physics of radiation deposition may take into account dose zone maps for different types of tissue. The value or values of one or more variables of the physics model are adjusted in the calibration. In yet another example, the dose model is formed as a transport model. Boltzmann type transport (e.g., diffusion) equations model the energy transport into and out of tissue. Different tissues may have different transport characteristics. The transport dose model may include relativistic adaptations. The value or values of one or more variables on the transport model are adjusted in the calibration.

Since the measured dose uses the dosimeter in the tissue mimicking object, the calibration may be specific to a type of tissue. The tissue mimicking object mimics or is made of the tissue of interest. The measured dose reflects the influence of the tissue in dose. The calibration accounts for the type of tissue. Similarly, the calibration is performed for a given isotope or isotopes. The calibration accounts for the isotope. By calibrating for the isotope used for a patient as well as the tissue of interest, a more patient-specific calibration is performed. By calibrating using the radiopharmaceutical to be used with the patient, a more accurate calibration for the patient may be provided.

The calibration may be repeated for different types of tissue. For example, the tissue mimicking object includes different materials mimicking different types of tissue. The dosimeters are positioned in the different materials. The same or different dose models are calibrated for the different types of tissue (e.g., dose kernels for bone, dose kernels for soft tissue, and dose kernels for fluid). Different or the same settings may result for the dose models of the different tissues. By calibrating for different types of tissue, the internal dose may be determined by type of tissue. The dose model as calibrated has different values for different tissues so that the dosing specific to different tissue regions may be more accurately determined.

The calibrated dose model more likely provides accurate dose estimation from measured emissions for a given radiopharmaceutical and corresponding isotope as compared to the dose model relying on simulation. Rather than using an uncalibrated or general dose model, the calibration provides for more accurate dose estimation with the calibrated dose model.

The calibration may be performed for different isotopes. The measurement and calibration of absorbed dose for defined tissues is provided for different isotopes and their spectra. A library of calibrated dose models by tissue type and isotope may be created. For patient-specific dosage determination, the calibrated dose models for the tissue type or types and isotope are selected and used. Alternatively, the calibration of dose is performed as part of the workflow for the patient, such as calibrating being performed for the patient. The internal dose is determined from the patient-specific calibrated dose model.

In act 58, the nuclear imaging system determines the internal dose for a patient with the calibrated dose estimation. The image processor or other processor determines the internal dose in the patient. The internal dose deposited by the radiopharmaceutical is calculated with the calibrated dose model. An amount of absorbed dose as a global value, by tissue-type, by tissue region, and/or by voxel is determined.

The image processor or another processor calculates an internal dose for a patient with the injected dose. After injecting the patient with the injected dose, the patient is scanned. Emissions are detected, such as with PET or SPECT. For example, the activity distributions are obtained from quantitative multi-modal SPECT at multiple time points either to initialize or to sample the time activity curve. A nuclear imaging scan of the patient is performed at different times. The resulting emissions are used to determine the internal dose over a given time or treatment. The dose by voxel and/or organ (i.e., tissue type) may be determined.

This internal dose is calculated using the dose model as calibrated. The dose model may be incorporated into reconstruction to reconstruct the dose. The dose model is fit as part of reconstruction. Alternatively, the dose model is fit to activity or uptake reconstructed at different times. The fit dose model is used to calculate the dose. The dose model and/or reconstruction may use the injected dose as a variable. Based on the injected dose and the calibrated dose model, the internal dose for the patient is determined from the detected emissions from within the patient.

The dose model is fit by location, such as by type of tissue, tissue region, and/or voxel. For each location, the calibrated dose model for the relevant type of tissue is used to determine the dose. In the embodiment reconstructing the dose as one reconstruction from emissions over time, the internal dose is reconstructed by location with the calibrated dose model(s) fit to data from the nuclear imaging scan in the reconstructing. For example, measured dose kernels for specific tissue types are included in a direct tomographic reconstruction, similar to a point spread function model for SPECT collimation. In the embodiment reconstructing activity distributions at different times, the internal dose is determined from the dose model after fitting the dose model to the activities over time (at different times) by location. Reconstruction and dose estimation employ the calibrated values for the different scenarios.

In act 59, the image processor or other processor estimates uncertainty of the internal dose. Error estimation and propagation in the calculation of the internal dose is performed. For example, the uncertainty estimation disclosed in U.S. Pat. No. 9,364,192 is used. Systematic error is estimated as a function of location. The systematic error is estimated by perturbing the system matrix. The values of one or more variables of the system matrix are altered, and the reconstruction repeated. The differences in the resulting object or image data of the different reconstructions provide systematic error information for dose calculation as a function of location. The uncertainty may be determined by perturbation of the internal dose estimation, such as altering values of calibration or other variables.

The image processor generates an image of the internal dose of the patient, and/or activity distribution of the patient. Any now known or later developed imaging for quantitative nuclear imaging may be used. After reconstruction, the output image object of dose distribution at a particular time, for a cycle, up to the current time, up to a last scan, and/or predicted for the not-yet occurring end of cycle is generated.

The image object is rendered or otherwise used to generate an image. For example, a multi-planar reconstruction or single slice image of a plane is generated. The intersection of one or more planes with the image object is visualized. As another example, a surface or projection rendering is performed for three-dimensional imaging. Other imaging may be used.

One image is generated. Alternatively, a sequence of images is generated. For example, image objects of internal dose at different time periods are used to generate a sequence of images representing the dosing in the patient over time.

The internal dose image may include uncertainty information. For example, a separate image showing distribution of uncertainty is displayed. As another example, a color or other overlay of uncertainty by location is added to the internal dose image. In yet another example, alphanumeric text, annotation, or other indication of a value of uncertainty is displayed, such as at a user selected location on the internal dose image or as a global uncertainty.

The dose image of the functional information from the reconstruction is displayed alone. Alternatively, an anatomical image is displayed with the functional image. For example, the functional image is overlaid on a CT image. The overlay may be dose colored for display on a gray scale CT image. Other combinations may be used, such as accumulated dose, uptake at a timepoint, and a CT image. An image of dose distribution and quantitative uptake may be generated and displayed.

For quantitative SPECT or PET, the image may be an alphanumeric text of a dose value for a location or a global dose. A graph, chart, or other representation of dose at multiple locations and/or times may be output. The spatial image representing distribution of dose may use color or brightness modulation to represent a level of dose by location. In one embodiment, the image is generated to show the average quantitative uptake by type of tissue.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for calibration of internal dose in a nuclear imaging system, the method comprising:
   detecting emissions from a radiopharmaceutical to be provided in a patient, the emissions detected with a solid-state detector;
   measuring a first dose of the radiopharmaceutical with a solid-state dosimeter;
   calibrating a dose model with the first dose and a second dose derived from the emissions;
   determining the internal dose in a patient by the radiopharmaceutical with the calibrated dose model.

2. The method of claim 1 wherein detecting the emissions comprises detecting from the radiopharmaceutical in a syringe or vial placed in a cavity, and wherein measuring the first dose comprises measuring with the solid-state dosimeter in a tissue mimicking object, the tissue mimicking object in the cavity with the syringe or vial.

3. The method of claim 2 further comprising estimating the second dose from the emissions with the dose model, and wherein calibrating comprises setting a value of a parameter of the dose model so that a difference between the first and second doses is minimized.

4. The method of claim 2 wherein calibrating comprises calibrating the dose model for a type of tissue mimicked by the tissue-mimicking tissue mimicking object.

5. The method of claim 1 wherein calibrating comprises setting a value of a parameter of the dose model so that a difference between the first and second doses is minimized.

6. The method of claim 1 wherein calibrating the dose model comprises calibrating for an isotope to be used for the patient in the radiopharmaceutical and a type of tissue, the calibrating being repeated for different types of tissue so that the dose model has different settings for the different types of tissue, and wherein determining the internal dose comprises determining by type of tissue using the dose model as calibrated for each type of tissue.

7. The method of claim 1 wherein the dose model comprises material dependent dose kernels, and wherein calibrating comprises adjusting the material dependent dose kernels.

8. The method of claim 1 wherein the dose model comprises a physics model of energy deposition, and wherein calibrating comprises adjusting the physics model.

9. The method of claim 1 wherein the dose model comprises a transport model, and wherein calibrating comprises adjusting the transport model.

10. The method of claim 1 wherein determining the internal dose comprises determining an absorbed dose in tissue of the patient.

11. The method of claim 1 further comprising estimating uncertainty of the internal dose and displaying the uncertainty and the internal dose.

12. The method of claim 1 wherein determining the internal dose comprises performing a nuclear imaging scan of the patient at different times and reconstructing the internal dose by location with the calibrated dose model fit to data from the nuclear imaging scan in the reconstructing.

13. The method of claim 1 wherein determining the internal dose comprises performing a nuclear imaging scan of the patient at different times, reconstructing activity from detected emissions of the nuclear imaging scans for each of the times, and fitting the calibrated dose model to the activities from the different times.

14. A method for calibration of internal dose in a nuclear imaging system, the method comprising:
   measuring a first dose induced to a first type of tissue by a first isotope;
   calibrating dose estimation to the measured first dose for the first type of tissue and the first isotope; and
   determining, by the nuclear imaging system, the internal dose for a patient with the calibrated dose estimation.

15. The method of claim 14 further comprising detecting emissions from a radiopharmaceutical in a syringe or vial and estimating a second dose from the emissions using the dose estimation, wherein measuring comprises measuring the first dose from the radiopharmaceutical in the syringe or vial with a solid-state dosimeter in a tissue mimicking object, the tissue mimicking object mimicking the first type of tissue, and wherein calibrating comprises altering the dose estimation based on the first and second doses.

16. The method of claim 14 wherein the dose estimation comprises a dose kernel model, a physics model, or an energy transport model, and wherein calibrating comprises setting a value of the dose kernel model, physics model, or energy transport model.

17. The method of claim 14 wherein measuring and calibrating is performed for different types of tissue including the first type and different isotopes including the first isotope.

18. The method of claim 14 wherein determining comprises detecting emissions from the first isotope in the patient, and fitting the calibrated dose estimation to activities from the emissions.

19. An emissions imaging system comprising:
- a tissue mimicking object with a solid-state dosimeter, the solid-state dosimeter configured to measure ionizing radiation from an isotope, and the tissue mimicking object configured to mimic a type of tissue;
- an image processor configured to calibrate a dose model from the measured ionizing radiation; and
- a nuclear imaging system configured to determine an internal dose for a patient using the calibrated dose model.

20. The emissions imaging system of claim 19 further comprising:
- a cavity configured to hold a syringe or vial and the tissue mimicking object; and
- a semiconductor detector adjacent the cavity and configured to detect emissions from within the syringe or vial within the cavity;
- wherein the image processor is configured to determine a first dose for the syringe or vial from the emissions and configured to calibrate based on the measured ionizing radiation and the first dose.

* * * * *